United States Patent
Southard

(10) Patent No.: US 6,500,198 B1
(45) Date of Patent: Dec. 31, 2002

(54) CRYSTAL QUARTZ SCEPTER

(76) Inventor: Barbara L. Southard, 70 Highland St., Middleboro, MA (US) 02346

( * ) Notice: Subject to any disclaimer, the term of this patent is extended or adjusted under 35 U.S.C. 154(b) by 63 days.

(21) Appl. No.: 09/664,446

(22) Filed: Sep. 18, 2000

Related U.S. Application Data

(60) Provisional application No. 60/157,116, filed on Oct. 4, 1999.

(51) Int. Cl.$^7$ ............................................... A61N 5/006
(52) U.S. Cl. ............................... 607/88; 607/90; 606/2
(58) Field of Search ...................... 607/88–95; 606/2.3; 128/898; 362/166, 169, 170, 174–178, 182, 186–188, 196

(56) References Cited

U.S. PATENT DOCUMENTS

| | | | |
|---|---|---|---|
| 3,527,932 A | | 9/1970 | Thomas |
| 4,658,823 A | * | 4/1987 | Beddoe et al. .............. 128/396 |
| 5,001,608 A | * | 3/1991 | Kehrli et al. ................. 362/19 |
| 5,309,337 A | * | 5/1994 | Groben ........................ 362/206 |
| 5,336,248 A | | 8/1994 | Good et al. |
| 5,359,685 A | * | 10/1994 | Waynant et al. .............. 385/35 |
| D372,276 S | | 7/1996 | Choi |
| 5,591,219 A | | 1/1997 | Dungan |
| 5,643,333 A | | 7/1997 | Yun |
| D386,807 S | | 11/1997 | Moonshine-Voelker et al. |
| 5,683,436 A | | 11/1997 | Mendes et al. |
| 5,782,825 A | * | 7/1998 | Anderson ..................... 606/15 |
| 5,843,074 A | | 12/1998 | Cocilovo |
| 5,961,543 A | * | 10/1999 | Waldmann ................... 607/88 |
| 5,968,033 A | * | 10/1999 | Fuller et al. ................... 606/9 |
| 6,158,871 A | * | 12/2000 | Geddes et al. .............. 362/118 |
| 6,161,845 A | * | 12/2000 | Baiardi ....................... 362/277 |

FOREIGN PATENT DOCUMENTS

WO    WO 89/03235    4/1989

* cited by examiner

Primary Examiner—Linda C. M. Dvorak
Assistant Examiner—Ahmed Farah
(74) Attorney, Agent, or Firm—Richard C. Litman

(57) ABSTRACT

A quartz crystal scepter which includes a conventional flashlight and a hollow casing which houses a lens, a concave washer, and a quartz crystal sphere. The flashlight and hollow casing may be one structure or separate structures that are attached. The quartz crystal scepter generates light energy of various colors which are filtered through a lens into a quartz crystal sphere. The quartz crystal sphere is rolled along the surface of a person's body part emitting a predetermined color of light. The second and third example of the quartz crystal scepter differ in how they are attached to the end of a flashlight.

7 Claims, 4 Drawing Sheets

CRYSTAL QUARTZ SCEPTER

CROSS-REFERENCE TO RELATED APPLICATION

This application claims the benefit of U.S. Provisional Patent Application Serial No. 60/157,116, filed Oct. 4, 1999.

BACKGROUND OF THE INVENTION

1. FIELD OF THE INVENTION

The present invention relates to a quartz crystal scepter. More specifically, the invention is directed to a quartz crystal scepter that directs a particular color of light onto the surface of a person's skin.

2. DESCRIPTION OF RELATED ART

The use of therapeutic light energy producing devices to assist in treating physical traumas to the human body is well known. The light produced by these devices are usually applied onto the surface of a person's body. Light energy is also used in many diagnoses of the developmental process in infants.

The following design patents illustrates different ornamental forms of scepters. U.S. Des. Pat. No. 372,276, issued to Chung-Hing Choi on Jul. 30, 1996, illustrates a toy scepter. The ornamental design of the toy scepter includes an elongated tubelike structure with both ends having fancy geometrical designs. U.S. Des. Pat. No. 386,807, issued to Moonshine-Voelker et al. on Nov. 25, 1997, illustrates a heart and star light. The ornamental design for the heart and star light is an elongated structure with one end having a fancy ornamental design that lights up.

The following patents describes many types of light energy producing devices for a variety of therapeutic treatments. U.S. Pat. No. 3,527,932, issued to James J. Thomas on Sept. 8, 1970, describes a transilluminating flashlight. The transilluminating flashlight comprises a portable battery operated flashlight having a light-impervious open ended tubular hood extending beyond the light emitting end of the flashlight.

The hood is formed of a self supporting but readily deformable material to enable a light fast seal to be made against a fragile substance such as the head of a newborn baby. The application of this patent is to determine if a newborn's skull is properly developed. This is achieved by placing the light directly against the infant's skull in a completely darkened room. The distribution of light within the infant's head determines the degree of development.

U.S. Pat. No. 5,001,608, issued to Kehrli et al. on Mar. 19, 1991, describes a therapeutic lamp which emits polarized light. The lamp comprises a housing of three consecutive parts which define a common interior space. The first part is a handle having a substantially tubular form. The second part is a dome-shaped middle portion attached to the end of the handle. The third part comprises a cylindrical frontal portion which is attached to the middle portion. A light source assembly and a light filter plate are enclosed within the housing for filtering out certain wavelengths of the ultraviolet spectrum. A fan is also included which forces in fresh air.

U.S. Pat. No. 5,336,248, issued to Good et al. on Aug. 9, 1994, describes a treatment and inhibition of retinopathy for premature eye development in newborns. The patent includes a component or system for producing only red light. The patient's head is received in a device which limits the light that reaches the patient's eyes.

U.S. Pat. No. 5,591,219, issued to Thomas E. Dungan on Jan. 7, 1997, describes a frequency modulator. This is a radiation device for therapeutic use onto the human body. The application of light waves are directed to affected areas of the body. A bulb produces the light source which is then passed through a s module having silicon and carbon granules. The device has a pistol-like housing which is designed to allow for the controlled application of radiation.

U.S. Pat. No. 5,643,333, issued to Young-Ung Yun on Jul. 1, 1997, describes a biological energy projector. The biological energy projector includes a photon producing means and produces photons from an outside power source. U.S. Pat. No. 5,683,436, issued to Mendes et al. on Nov. 4, 1997, describes a treatment for Rhinitis by biostimulative illumination. The illumination device includes at least one light emitting diode pack for insertion into at least one affected nostril.

U.S. Pat. No. 5,843,074, issued to Tony Cocilovo on Dec. 1, 1998, describes a therapeutic device using pulsed and colored light which is emitted onto living creatures. Pulsed and colored light is applied to local areas by means of a small diameter optic fiber housed in a pen-like handpiece which makes the application of the device precise.

The problem with the inventions disclosed in the patents mentioned above is that they are either very expensive or difficult to operate. The ideal illumination device would fit any light source such as a conventional flashlight and would be made of materials that are sturdy but inexpensive. It has been shown that devices that roll along the surface of the skin on a person's body is also therapeutic. Therefore, a device which illuminates and applies rolled pressure onto the surface of a person's body would be novel.

None of the above inventions and patents, taken either singly or in combination, is seen to describe the instant invention as claimed.

SUMMARY OF THE INVENTION

The quartz crystal scepter comprises a conventional flashlight and a hollow casing which houses a lens, a concave washer, and a quartz crystal sphere. The flashlight and hollow casing may be one structure or separate structures that are attached. The quartz crystal scepter generates light energy of various colors which are filtered through a lens into a quartz crystal sphere. The quartz crystal sphere is rolled along the surface of a person's body part emitting a predetermined color of light. The second and third examples of the quartz crystal scepter differ in how they are attached to the end of a flashlight.

Accordingly, it is a principal object of the invention to provide a quartz crystal sphere that permits light energy to be rolled onto the surface of a person's body.

It is another object of the invention to provide a variety of illuminating devices each with a desired color of light to be applied to the surface of a person's body.

It is a further object of the invention to provide a hollow casing that is easily attached to the end of a conventional flashlight.

Still another object of the invention to provide an illumination device that generates a desired color of light to be applied to the surface of a person's body.

It is an object of the invention to provide improved elements and arrangements thereof a quartz crystal scepter in an apparatus for the purposes described which is inexpensive, dependable and fully effective in accomplishing its intended purposes.

These and other objects of the present invention will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

Figure 1:
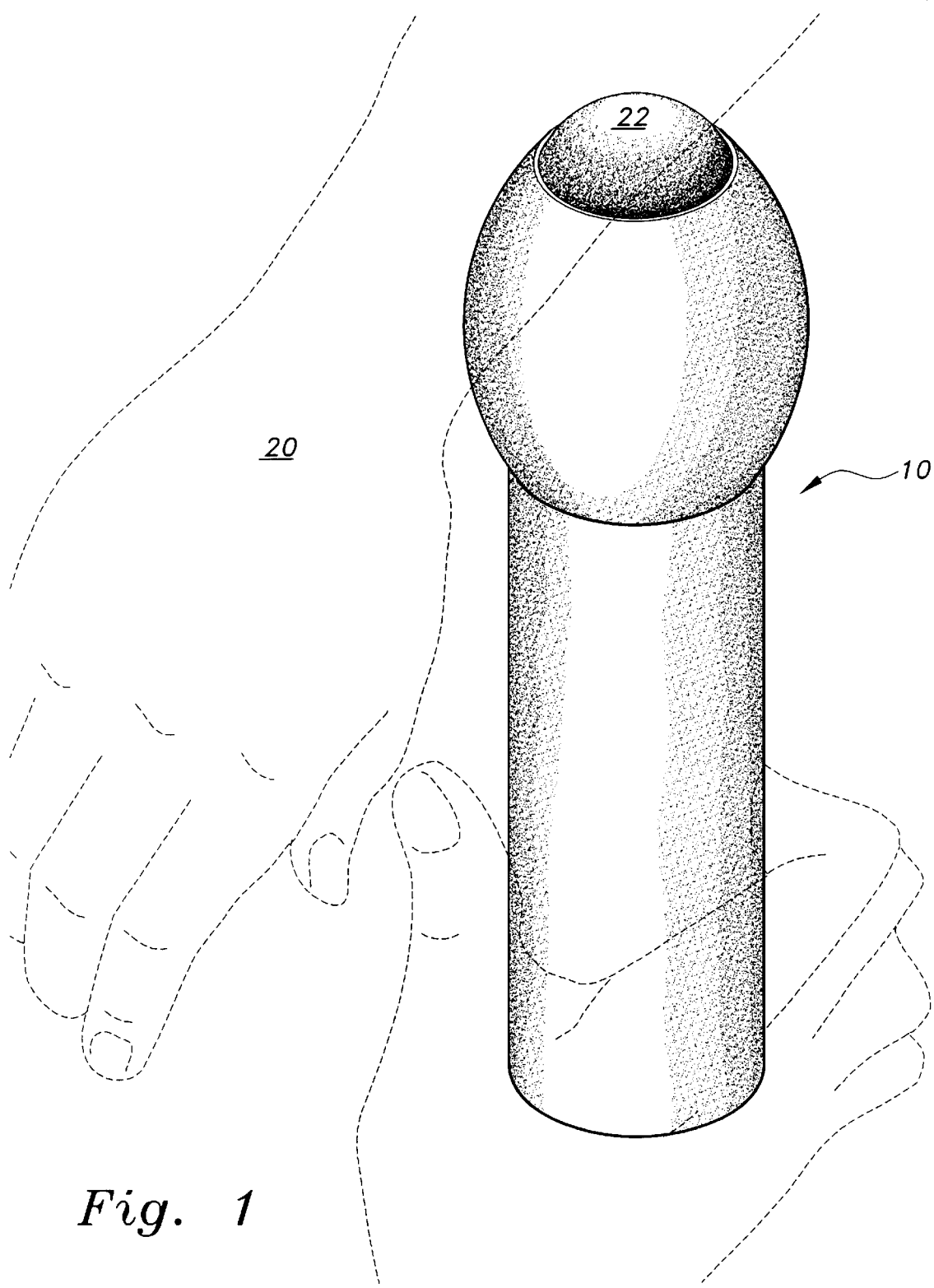
FIG. 1 is an environmental, perspective view of quartz crystal color scepter according to the present invention.

The present invention is a quartz crystal scepter designated as 10 in the drawings. The quartz crystal scepter comprises a conventional flashlight and a hollow casing which houses a lens, a concave washer, and a spherical quartz crystal.

FIG. 1 illustrates the operation of the quartz crystal scepter 10 being applied to the surface of a person's skin 20. The quartz crystal scepter 10 generates light energy of various colors which are filtered through a lens (not shown) into a quartz crystal sphere 22. The quartz crystal sphere 22 rolls along the surface of a person's body part 20 emitting a predetermined color of light.

Figure 2:
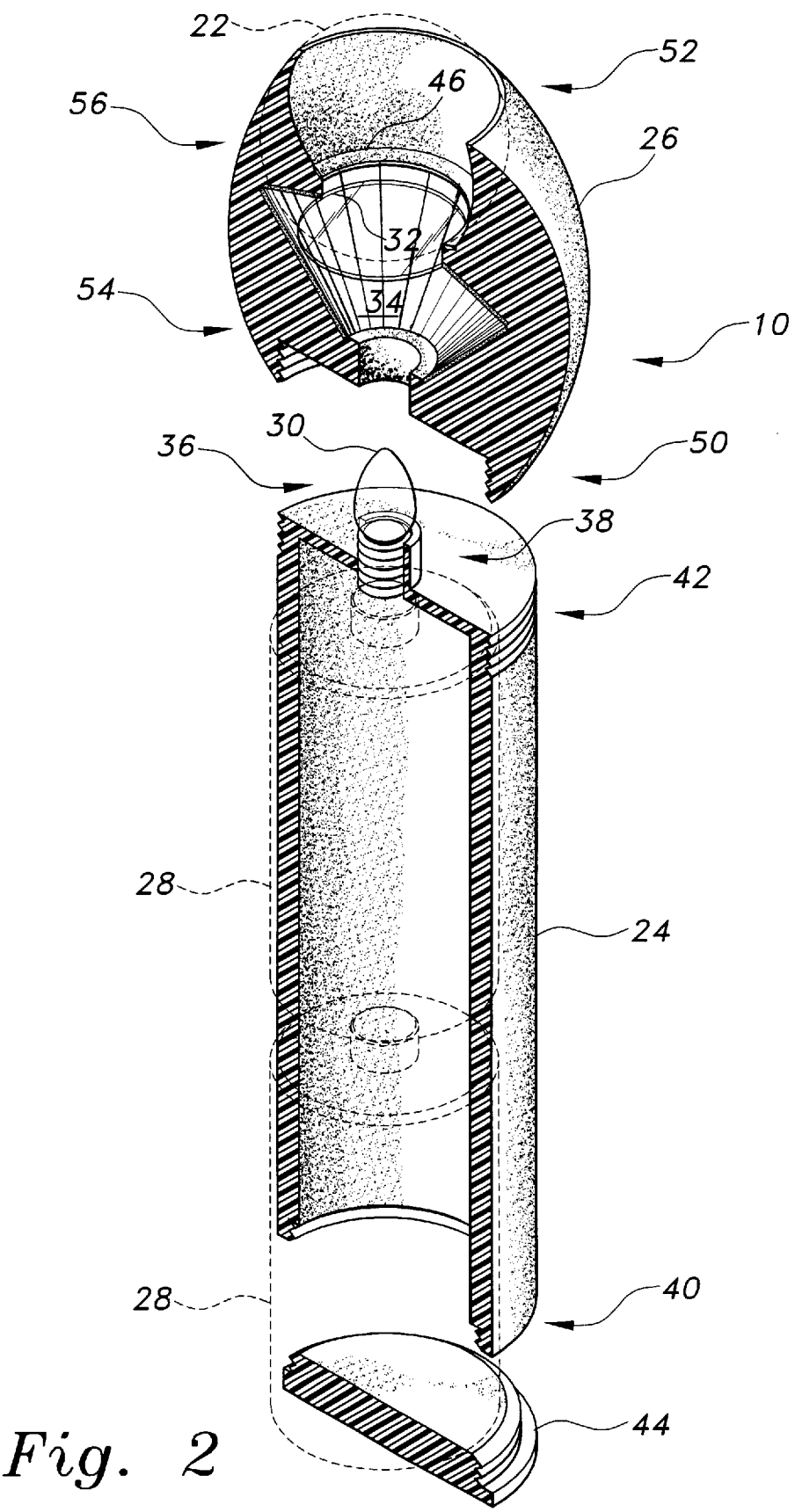
FIG. 2 is a sectional view of the first example of the quartz crystal color scepter of the present invention.

FIG. 2 illustrates the first example of the quartz crystal scepter 10. The quartz crystal scepter 10 comprises a rear section 24 (flashlight) and a front section 26 (hollow casing). The rear section 24 comprises a conventional flashlight having a tube-like structure that houses the batteries 28, bulb 30, lens 32, and a reflective element 34. The reflective element 34 surrounds the bulb 30 to intensify the emission of light generated from the bulb 30. The conventional flashlight 24 generates the needed light source and also acts as a handle for the present invention 10.

Depending on the configuration of the flashlight 24 the reflective element 34 may be housed in the hollow casing 26 or housed within the flashlight 24. The flashlight 24 houses the bulb 30 and batteries 28 needed to generate a light source. The bulb 30 has a top portion 36 and a bottom 38 portion. The bottom portion 38 of the bulb 30 is securely seated in the flashlight 24. The top portion 36 of the bulb 30 extends into the hollow casing 26. Alternative type bulbs 30 may be used but the preferred bulb 30 emits a continuous white light.

The flashlight 24 comprises a first end 40 and a second end 42. The first end 40 is capped and the second end 42 receives the bottom portion 38 of the bulb 30. The second end 42 is dimensioned and configured to threadingly fit the threaded the hollow casing 26, while the first end 40 is dimensioned and configured to threadingly fit a removable cap 44. A removable cap 44 at the first end 40 of the flashlight 24 permits the batteries 28 and bulb 30 to slide out and be replaced when needed.

The essence of the present invention 10 involves the structure and application of the hollow casing 26. The front section 26 of the quartz crystal scepter 10 comprises a hollow casing 26 which houses a color lens 32, a concave washer 46, a reflective region 34, and a quartz crystal sphere 22. The hollow casing 26 comprises a first end 50 and a second end 52. The hollow casing 26 comprises first end which is dimensioned and configured to threadingly fit the end of the flashlight 24 and the second end 52 is dimensioned and configured to house a major portion of the quartz crystal sphere 22.

The front section 26 of the quartz crystal scepter 10 comprises a first 54 and second 56 region. The first region 54 is dimensioned and configured to receive an optional reflective element 34 and the top portion 36 of the bulb 30. The reflective element 34 surrounds the top portion 36 of the bulb 30 and acts to enhance or increase light intensity when directed into the colored lens 32 and quartz crystal sphere 22. The light source in most conventional flashlights 24 are turned off and on in three ways: by twisting the capped end 40 of the flashlight 24, by a push button switch, or by twisting the threadingly engaged hollow casing 26 further onto the 42 end of the flashlight 24. The present invention 10 is capable of fitting all three types of flashlights 24.

The second region 56 of the hollow casing 26 is dimensioned and configured to receive a colored lens 32, a concave washer 46, and a quartz crystal sphere 22. The shape of the hollow casing 26 may come in many alternate forms as long as it does not alter the inventiveness of the invention 10. The colored lens 32 sits above the top portion 36 of the bulb 30 and directly beneath the concave washer 46. The colored lens 32 is dimensioned and configured to allow a particular color of light pass through the lens 32 while the remaining colors are filtered out.

Lenses 32 will vary according to the particular color which depends on the trauma or type of treatment being used. The lenses 32 will differ in color such as red, white, blue, green, orange, purple, yellow, or any other color that would be translucent. The different colored lenses 32 not only alter the frequency of the light waves, but also filter out certain light frequencies. Each hollow casing 26 comes with a removable (not shown) or non-removable colored lens 32.

The second end 52 of the hollow casing 26 is dimensioned and configured to receive a major portion of the quartz crystal sphere 22 and is shaped to permit the quartz crystal sphere 22 to roll within the second end 52 of the hollow casing 26. A quartz crystal sphere 22 rollingly sits within the concave washer 46. It has been shown that devices that roll along the surface of the skin on a person's body is also therapeutic. Therefore, the quartz crystal sphere 22 has two functions. The first function acts to apply light energy along the surface of the skin of a person's body. The second function applies rolled pressure onto the surface of a person's body parts.

The concave washer 46 is comprised of a material that will not damage the quartz crystal sphere 22 when it is being rolled within the hollow casing 26. The hollow casing 26 is made of a sturdy, dark colored, durable material which prevents the loss of light that might pass through if the hollow casing 26 were translucent. The second 12 and third 14 examples of the quartz crystal scepter shown in FIGS. 3 and 4 differ in how they are attached to the end 42 of a flashlight 24. The flashlight 24 and hollow casing 26 may be one structure or separate structures that are attached.

Figure 3:
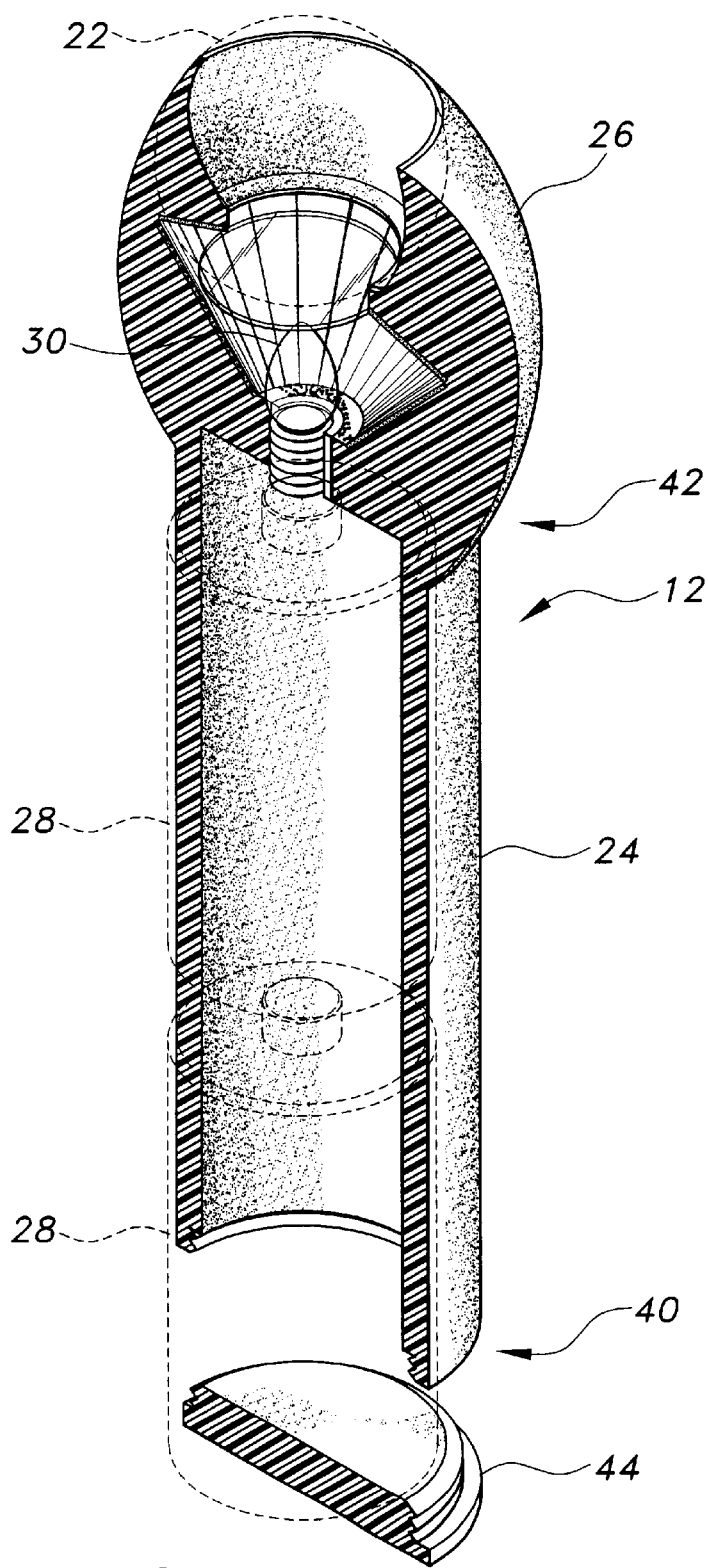
FIG. 3 is a sectional view of the second example of the quartz crystal color scepter of the present invention.

FIG. 3 illustrates the second example 12 of the quartz crystal scepter 10. In this example of the present invention 12 the hollow casing 26 and the flashlight 24 are dimensioned and configured to be formed of a unitary construction. The end 40 of the flashlight 24 must be capped 44 in this example 12 in order to remove and replace the bulb 30 and batteries 28 when needed.

Figure 4:
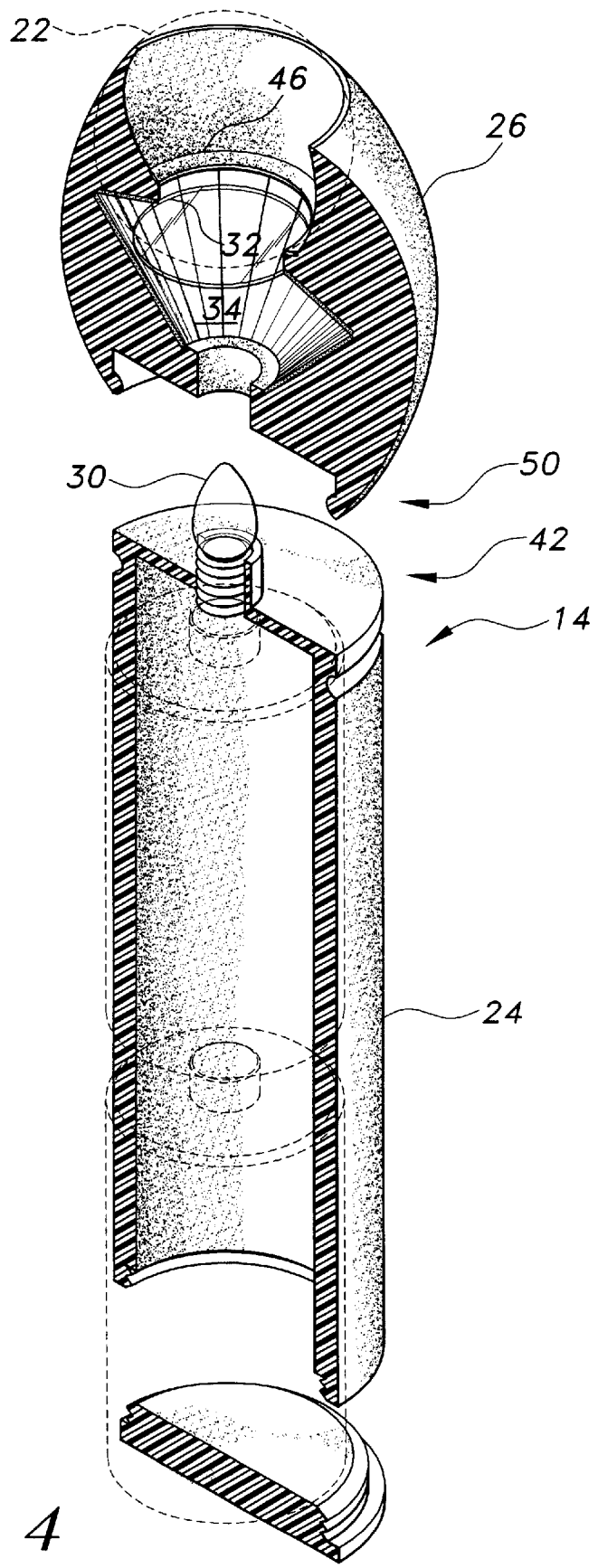
FIG. 4 is a sectional view of the third example of the quartz crystal color scepter of the present invention.

FIG. 4 illustrates the third example 14 of the quartz crystal scepter 10. The end 50 of the hollow casing 26 is preferably molded in such a manner that the inner portion conforms and frictionally engages to the shape of the end 42 of the flashlight 24. The end 42 of the flashlight is threaded and the diameter of the end 50 of the hollow casing 56 is slightly larger than the end 42 of the flashlight 24. The bulb 30, lens 32, concave washer 46, reflective element 34, and quartz crystal sphere 22 are not changed within the hollow casing 26 as described in the first example 10 of the present invention.

It is to be understood that the present invention is not limited to the embodiments described above, but encompasses any and all embodiments within the scope of the following claims.

I claim:

1. A therapeutic light-emitting scepter comprising:

a tubular housing for containing a source of electrical power, said housing having a capped first end and a second end;

a spherical casing having a lower portion attached to the second end of said housing and an opposite upper portion defining a circular opening therein, said casing including a centrally disposed bulb adjacent the first portion, a reflective element surrounding said bulb, a lens positioned above said reflective element and a concave washer positioned above said lens; and a quartz crystal sphere rotatably supported by said concave washer and substantially housed within said spherical casing such that a portion of said quartz crystal sphere rollably protrudes through the circular opening of said casing; whereby, upon application of the therapeutic light-emitting scepter to a person's skin surface and activation of the bulb, light energy is emitted through the lens and out the quartz crystal sphere as it rolls within the casing while being applied to the person's skin surface.

2. The therapeutic light-emitting scepter according to claim 1, wherein said spherical casing is threadingly attached to the second end of said housing.

3. The therapeutic light-emitting scepter according to claim 1, wherein said spherical casing is integrally connected at the second end of said housing.

4. The therapeutic light-emitting scepter according to claim 1, wherein said bulb emits a continuous white light.

5. The therapeutic light-emitting scepter according to claim 1, wherein said scepter is battery operated.

6. The therapeutic light-emitting scepter according to claim 1, wherein said lens is colored to emit a colored light through said quartz crystal sphere.

7. The therapeutic light-emitting scepter according to claim 6, wherein said lens is replaceable by differently colored lens.

* * * * *